United States Patent [19]
Klein et al.

[11] Patent Number: 5,928,231
[45] Date of Patent: Jul. 27, 1999

[54] IMPLANTABLE OSTEOSYNTHESIS DEVICE

[76] Inventors: Jean-Michel Klein, 31 bis rue Ambroise Thomas, 31400 Toulouse; Michel Trouillet, 1065 chemin du Jouliou, 31600 Eaunes, both of France

[21] Appl. No.: 08/952,152

[22] PCT Filed: May 10, 1996

[86] PCT No.: PCT/FR96/00706

§ 371 Date: Nov. 12, 1997

§ 102(e) Date: Nov. 12, 1997

[87] PCT Pub. No.: WO96/36291

PCT Pub. Date: Nov. 21, 1996

[30] Foreign Application Priority Data

May 19, 1995 [FR] France ................................ 95 06089

[51] Int. Cl.$^6$ ............................................. A61B 17/68
[52] U.S. Cl. ............................... 606/60; 606/61; 606/67; 606/72; 606/218
[58] Field of Search ................................ 606/53–58, 60, 606/61, 72, 74, 151, 157, 158, 213, 215, 216, 218; 600/232; 74/575, 578; 254/11, 12; 269/143, 166, 169, 249

[56] References Cited

U.S. PATENT DOCUMENTS

| 153,206 | 7/1874 | Van Wagoner . |
| 845,665 | 2/1907 | Ramsden . |
| 1,689,331 | 4/1928 | Disibio . |
| 2,199,949 | 5/1940 | Davis . |
| 4,257,409 | 3/1981 | Bacal et al. ........................... 606/61 |
| 4,279,248 | 7/1981 | Gabbay . |
| 5,478,340 | 12/1995 | Kluger . |

FOREIGN PATENT DOCUMENTS

| 0 301 898 | 2/1989 | European Pat. Off. . |
| 0 553 782 | 8/1993 | European Pat. Off. . |
| 2 208 476 | 4/1989 | United Kingdom . |

Primary Examiner—Michael Buiz
Assistant Examiner—David O. Reip
Attorney, Agent, or Firm—Young & Thompson

[57] ABSTRACT

An implantable osteosynthesis device is made up of two portions, a so-called fixed portion and a movable portion, which can move relative to each other and are provided with coupling elements capable of blocking the translation of the portions so as to obtain a clamping effect on the bone, wherein the fixed portion has an elongated element (1) and the movable portion has a body (5) forming a sleeve (6) capable of sliding along the elongated element. The coupling of the invention comprise one-way combined locking arrangements (2, 10–13) for allowing the relative displacement of the fixed and movable portions in a single direction adapted for providing the clamping effect, and for locking the portions so as to prevent the translation thereof in the other direction.

15 Claims, 6 Drawing Sheets

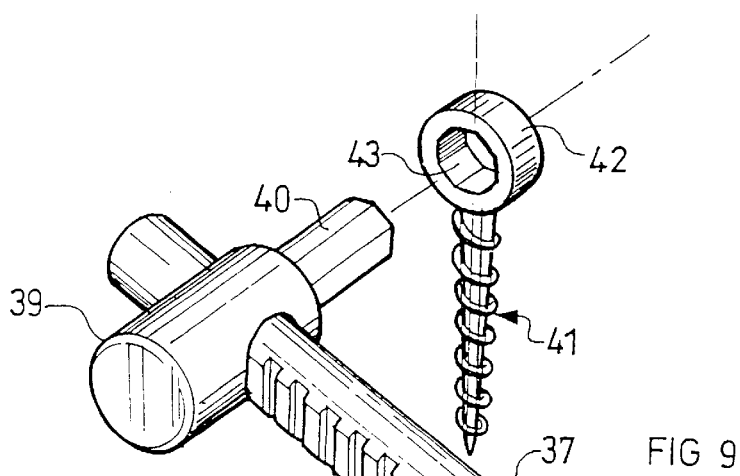
FIG 9
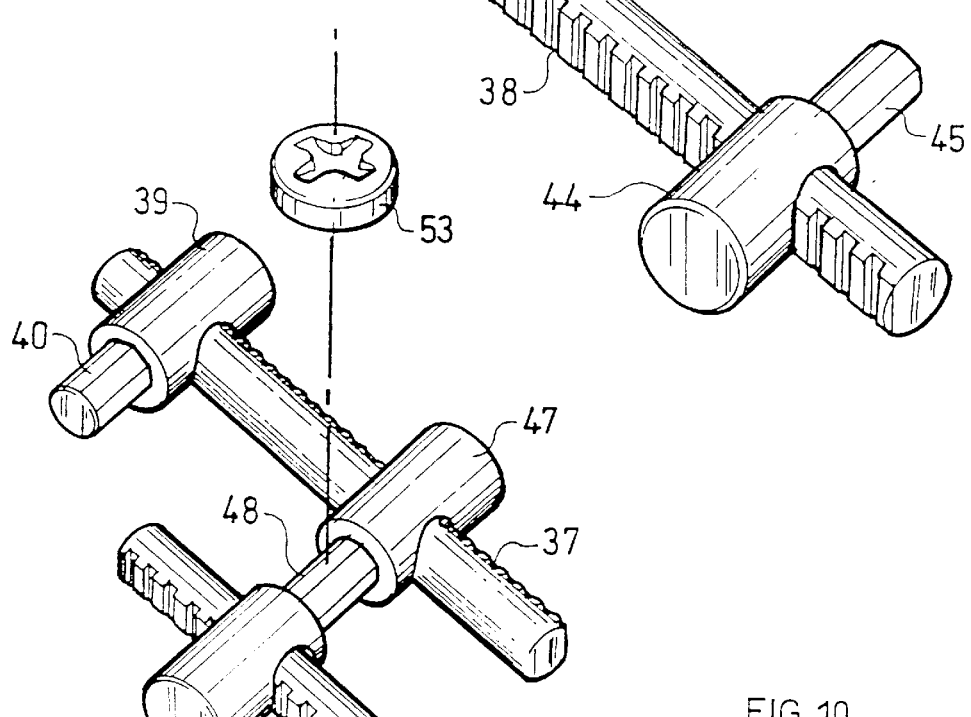
FIG 10
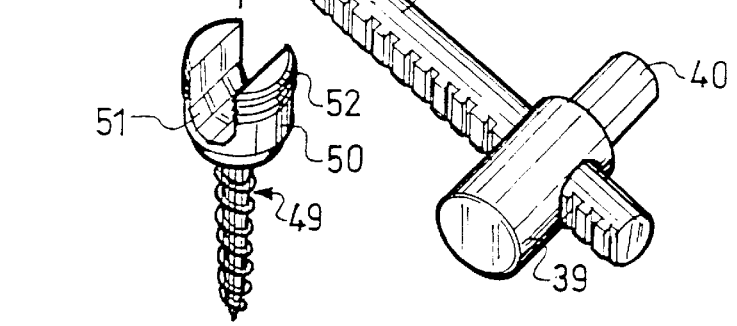

_

IMPLANTABLE OSTEOSYNTHESIS DEVICE

FIELD OF THE INVENTION

The invention concerns an implantable osteosynthesis device.

BACKGROUND OF THE INVENTION

The essential objective of every implantable osteosynthesis device consists in the production of a clamping effect on the bony parts capable of guaranteeing an effective strengthening of the bone. For that purpose, all of the present devices for osteosynthesis are designed to possess, once implanted, a solidity and a rigidity which make it possible to guarantee the production of a perfect clamping effect. However, it turns out that in order to satisfy this objective, all of the solutions proposed have led to the design of osteosynthesis devices whose implantation requires a long and complex operational procedure and considerable ancillary instrumentation.

Thus, for example, in the context of osteosynthesis of the sternum in particular for the purpose of the closure of a sternotomy, currently used equipment consists of so-called COTREL-DUBOUSSET clamps comprising a first hook fixed to a threaded bar, a second hook designed to slide in the direction of the fixed hook, and means for blocking translational and rotational movement of this second hook comprising a screw nut/lock nut system and a locking screw introduced into the base of said second hook.

Although the clinical experiments demonstrated the reliability of this equipment which makes it possible to obtain good bone strengthening, the operating procedure for the implantation of the latter proves, on the other hand, to be relatively complex and difficult. In fact, this implantation requires the use of an adjustable clamp designed to ensure the sliding of the movable hook until the hooks are subject to compression, then while maintaining this compression, requires the blocking of the movable hook be ensured in the first place by means of the screw nut/lock nut system, and in the second place by means of the locking screw. Subsequently, the surplus bar must be cut by means of a wire cutter, and the head of the locking screw must also be cut so that it does not project.

In practice, it turns out that the implantation of two or three clamps, necessary for the osteosynthesis of the sternum requires a not inconsiderable period of time of about a quarter of an hour. Furthermore, it should be noted that such clamps are not completely reliable owing to the fact that the locking screw cannot guarantee absolutely the blocking of the rotation of the movable hook.

SUMMARY OF THE INVENTION

The present invention aims to remedy the disadvantages of the present devices for osteosynthesis previously mentioned and its principal objective is to provide an osteosynthesis device, the operating procedure for the implantation of which, on the one hand, is very simple and very easy and requires minimal ancillary instrumentation and which, on the other, makes it possible to obtain a perfect clamping effect on the bony parts.

Another objective of the invention is to provide a compressive and distractive device for osteosynthesis.

Another objective of the invention is to provide an osteosynthesis device which enables an osteotomy to be performed very easily.

For this purpose, the object of the invention is an implantable osteosynthesis device comprising two parts, called fixed and movable, one movable relative to the other and equipped with coupling means capable, on the one hand, of conferring on them this property of relative movement and, on the other, of blocking them relatively in translation so as to obtain a clamping effect on the bone:

the fixed part comprising an elongated element, the movable part comprising a body forming a sleeve capable of sliding the length of the elongated element, and the coupling means comprising coupled one-way locking means, respectively incorporated into one of the parts, fixed or movable, and arranged on the other, capable of allowing the relative displacement of said parts in one direction of displacement only appropriate for making possible the clamping effect, and of locking in translation these fixed and movable parts in the other direction of displacement.

According to the invention, this device for osteosynthesis is characterized in that the one-way locking means comprises a number of parallel notches arranged on the elongated element of the fixed part, and a ratchet system incorporated into the body of the movable part, comprising an asymmetric tooth combined with elastic means and adapted to lock into the notches of the elongated element with a clearance capable of allowing the ratchet system and the body to tilt with respect to said elongated element so as to produce a wedge effect ensuring self-locking.

In the first place, the operating procedure for the implantation of such an osteosynthesis device is very simple and rapid because the blocking in translation of the fixed and movable parts is obtained automatically and instantaneously upon the relative displacement of said fixed and movable parts owing to the one-way character of the incorporated locking means with which these latter are equipped.

As a result, this implantation simply requires the relative displacement of the fixed and movable parts until the desired clamping effect is obtained and which proves in addition to be irreversible and definitive, then if necessary the sectioning of the surplus of the elongated element in the case of applications in which this surplus may be troublesome.

Such a design thus leads, on the one hand, to an appreciable saving of time compared with the operating procedures for the implantation of the known osteosynthesis devices and, on the other, to an extreme simplication of the necessary ancillary instrumentation.

Furthermore, such a device for osteosynthesis may be used for the purpose of compressive or distractive osteosyntheses depending on the direction of relative displacement of the fixed and movable parts allowed by the locking means.

In the second place, the only function of the asymmetric tooth of the one-way locking means is to ensure the maintenance in position of the movable part, the efforts applied to this latter tending to lead to a wedge effect which leads to the self-locking of said movable part. As a result, the relatively small size of the locking means does not render the osteosynthesis device more fragile which, owing to the self-locking phenomenon, proves to possess a rigidity, a solidity and a reliability guaranteeing a perfect clamping effect.

According to another characteristic of the invention, the asymmetric tooth extends in projection with respect to one of the faces, the so-called upper face, of a pawl and comprises an inclined front face capable of allowing the displacement of the movable part in a direction of displacement and an opposite front face capable of blocking in translation the said movable part, the portion of the upper face of the pawl adjacent to the inclined face of the asymmetric tooth extending at a lower level than the portion of said upper face adjacent to the blocking face of said asymmetric tooth.

Such a design in fact makes it possible to easily control the tilting clearance leading to the self-locking effect so as to obtain this effect while ensuring the maintenance in position of the asymmetric tooth within the corresponding notch.

Moreover, the body of the movable part comprises advantageously a housing opening radially into the sleeve capable of accommodating the ratchet system.

Furthermore, in order to form the housing of the ratchet system, a bore arranged transversally with respect to the sleeve is preferentially drilled through the body of the movable part starting from one of the external faces of said body, so as to form said housing opposite to said external face with respect to said sleeve.

In addition, according to another characteristic of the invention:

a bore arranged transversally with respect to the sleeve is drilled through the body of the movable part from one of the external faces of said body so as to open into the bottom of the housing of the ratchet system, said bore possessing a cross-section smaller than that of said housing, the ratchet system comprises, opposite to the asymmetric tooth, an axis of dimensions suitable for extending into the bore and of opening to the exterior of the body of the movable part, said axis being equipped at its open end with a control device capable of making it possible to swivel on itself.

Such an arrangement has the advantage of making possible by means of the same device a compressive and/or distractive osteosynthesis by orienting the ratchet system appropriately through the intermediary of the control device. In addition, it makes possible the adjustments of the relative position of the movable part as well as the disassembling of the device.

Furthermore, this arrangement proves particularly advantageous for operations such as osteotomy, surgery of the spine, . . . which require first the separation of two parts of the bone in order to implant grafts, then the compression of these parts of the bone in order to make osteointegration possible. In fact, and as should be more intelligible hereafter, these two operations may be performed without requiring instrumentation (heavy toothed forceps, . . . ) such as is used at present, the separation then the compression being obtained successively by means of a single osteosynthesis device, with inversion of the position of the ratchet system between these two operations.

According to a first preferred embodiment of the invention relating to an osteosynthesis device particularly designed for the strengthening of the sternum, in particular after sternotomy or for the cervical spine:

the fixed part comprises an elongated element constituted of a rectilinear bar and linking means comprising a body forming one piece with one of the ends of the rectilinear bar and an attachment piece extending in the prolongation of said body and having the form of a hook able to unite with a bone, the movable part comprises an attachment piece extending in the prolongation of the body of said movable part and having the form of a hook similar to that of the fixed part and arranged to extend in parallel with this latter.

Furthermore, and advantageously, the rectilinear bar comprises longitudinally at least one flat surface, the sleeve arranged in the body of the movable part having a cross-section adapted to that of said rectilinear bar.

This form of the rectilinear bar guarantees in fact a blocking of the relative rotation of the fixed and movable parts.

According to a second preferred embodiment relating to an osteosynthesis device particularly designed for long bones such as the femur, tibia, humerus, . . . but also capable of being used for strengthening the sternum:

the fixed part comprises an elongated element constituted of a rectilinear rigid blade curved at one end so as to form a bend of 180 degrees able to unite with a bone, the movable part comprises an attachment piece borne by the body of said movable part and constituted of a rigid bent blade forming a bend of 180 degrees, coupled with that of the rigid blade of the fixed part, arranged so as to extend in parallel with this latter, said bend being displaced laterally with respect to the longitudinal axis of the elongated element of the fixed part.

According to a third preferred embodiment relating to an osteosynthesis device particularly designed for a trochanteric or olecranal osteosynthesis:

the fixed part comprises an elongated element constituted of a cylindrical spindle equipped with a pointed end and comprising an annular groove near to this end, and an attachment piece having the form of a claw equipped with a body comprising a transverse neck able to lodge itself in the annular groove of the spindle, the movable part comprises an attachment piece extending in the prolongation of the body of said movable part and having the form of a claw similar to that of the fixed part and arranged to extend in parallel with this latter.

According to another preferred embodiment relating to an osteosynthesis device particularly designed for performing osteotomies:

the fixed part comprises an elongated element constituted of a rigid blade having two parallel rectilinear end-sections connected by a central section inclined with respect to the longitudinal axis of these latter, one of said end-sections having an aperture capable of accommodating a screw head, and the other end-section being equipped with locking means, the movable part comprises at least one attachment piece able to penetrate a bone.

In addition, in this case, when the ratchet system is combined with a control device making it possible to alter its orientation, the operations of separation followed by compression of the bony parts may be performed after precutting of the bone and implantation of the screw and the attachment piece, without requiring additional instrumentation.

According to another preferred embodiment relating to an osteosynthesis device particularly designed for spinal surgery:

the fixed part comprises an elongated element constituted of a rectilinear bar and linking means consisting of a body mounted on said elongated element prolonged by an axis of polygonal cross-section, and an attachment piece consisting of a pedicular screw equipped with a head through which is drilled a slot of polygonal cross-section adapted to that of the body axis, the movable part comprises linking means consisting of an axis of polygonal cross-section extending in the prolongation of the body of said movable part, in parallel with the axis of the linking means of the fixed part, and an attachment device consisting of a pedicular screw equipped with a head through which is drilled an aperture of polygonal cross-section conjugated with that of said axis.

Such a device makes it possible, from the anchoring points, to place each element in a situation of traction or distraction-compression thus allowing, apart from the reduction of the anatomical deformations, a prestressing of the osteosynthesis system which increases its mechanical resistance to the demands to which the diseased vertebral segments are subjected.

Furthermore, the polygonal form of the axes and slots of the screw heads offer several possibilities for rotational adjustment (function of the number of faces of the polygon) which allows the fixed part to tilt in the sagittal plane so as to obtain a reduction of the anatomical deformations of the lordosis or kyphosis type.

According to another characteristic of the invention relating to an osteosynthesis device designed for spinal surgery and making it possible to perform a framework assembly which increases appreciably the resistance of the entire device, the latter comprises two devices for spinal osteosynthesis such as described above arranged in parallel, and an osteosynthesis device equipped with hooks or linking devices in the form of 180 degrees bend, such as described above, arranged so as to connect the elongated elements of the two osteosynthesis devices previously mentioned.

According to another characteristic of the invention relating to an osteosynthesis device designed for spinal surgery and making it possible to carry out a multistage assembly comprising three anchoring points, this latter comprises:

a fixed unit composed of two fixed parts each consisting of an elongated element constituted of a rectilinear bar and linking means comprising a body mounted on said elongated element, towards one of the ends of this latter, prolonged by an axis of polygonal cross-section, and an attachment piece consisting of a pedicular screw equipped with a head drilled through which is drilled a slot of polygonal cross-section adapted to that of the axis of the body, a movable intermediate unit for linking the elongated elements of the fixed unit in the region of a section of these latter opposite to the end bearing the linking means, adapted so that the said elongated elements extend in parallel by being partially displaced longitudinally, said intermediate movable unit comprising a movable part mounted on each elongated element, and linking means comprising, on the one hand, an axis of polygonal cross-section connecting the bodies of said movable parts and extending at right angles to the elongated elements and, on the other hand, an attachment piece consisting of a pedicular screw equipped with a head possessing a groove of polygonal cross-section adapted to that of said axis and an external thread in the upper part and of a cap capable of being screwed on to the upper part of said head.

Moreover, in the context of the applications of the invention to spinal surgery, the body of the linking means of each fixed part may advantageously comprise one-way locking means capable of making it possible to deplace it in only one direction of displacement relative to the corresponding elongated element.

BRIEF DESCRIPTION OF THE DRAWINGS

Other characteristics, objectives and advantages of the invention will become apparent from the detailed description which follows with reference to the appended drawings which represent, as non-limiting examples, seven preferred embodiments and one variant of an embodiment. On these drawings which form an integral part of the present description:

FIG. 9 is a perspective view of a fifth embodiment of an osteosynthesis device in conformity with the invention designed for spinal surgery, FIG. 10 is a perspective view of a sixth embodiment of an osteosynthesis device in conformity with the invention also designed for spinal surgery.

DESCRIPTION OF THE PREFERRED EMBODIMENTS

Figure 1:
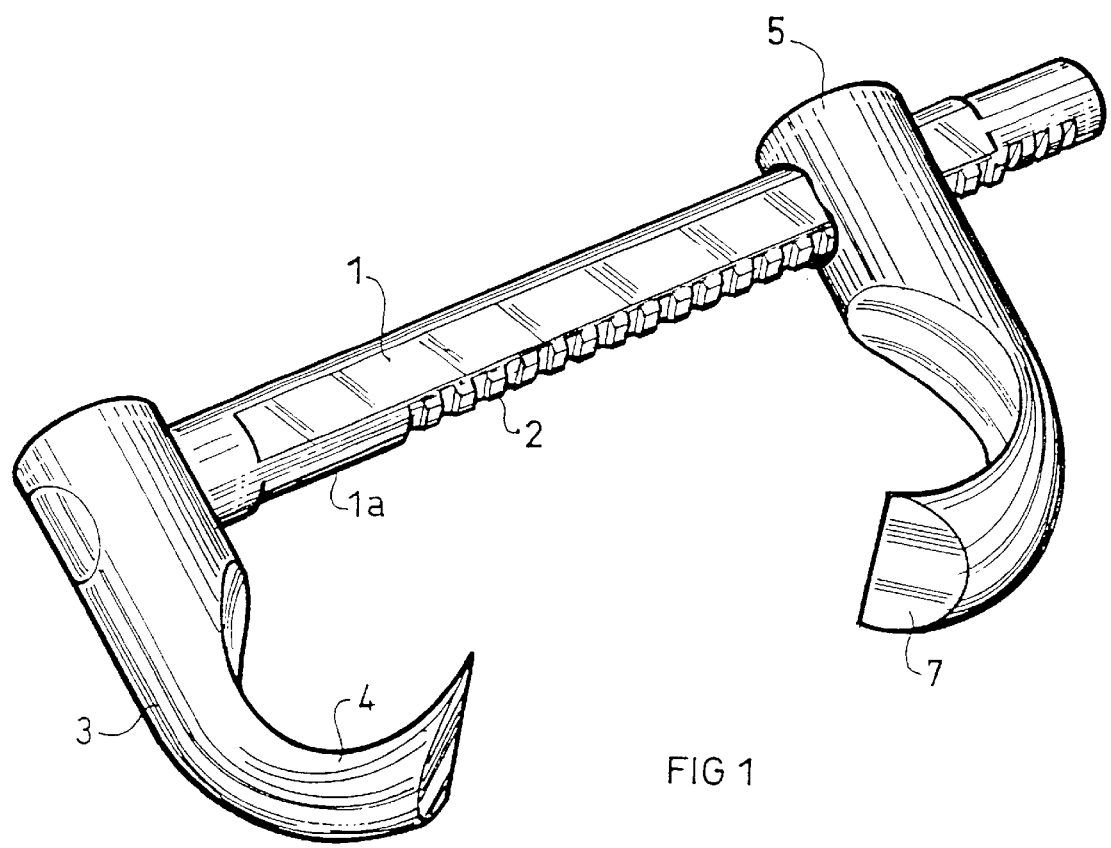
FIG. 1 is a perspective view of a first embodiment of an osteosynthesis device in conformity with the invention designed for the osteosynthesis of the sternum or for cervical spine surgery.

The osteosynthesis devices represented in FIGS. 1 to 11 all comprise a so-called fixed part equipped with means for linkage to a bone, a so-called movable part also equipped with means for linkage to a bone, as well as combined locking means capable of making possible the relative displacement of said fixed and movable parts in only one direction of displacement and to ensure their self-locking in the other direction of displacement.

In the first place, the device shown in FIGS. 1 to 4 is designed in particular for the osteosynthesis of the sternum after sternotomy, or as a preventive measure in the case of sternal dehiscences as well as for the surgery of the cervical spine.

The fixed part of this osteosynthesis device comprises a rigid bar 1 of approximately square cross-section, one so-called lower face of which 1a, comprises transverse notches 2 which start at one of the ends of said bar and extend over approximately three quarters of its length.

This fixed part comprises, in addition, at the end lacking notches 2, means for linkage consisting of a cylindrical body 3 through which is drilled a radial bore and which is attached to the bar 1 and in the longitudinal extension of said cylindrical body, an attachment piece in the form of a hook 4.

Figure 2:
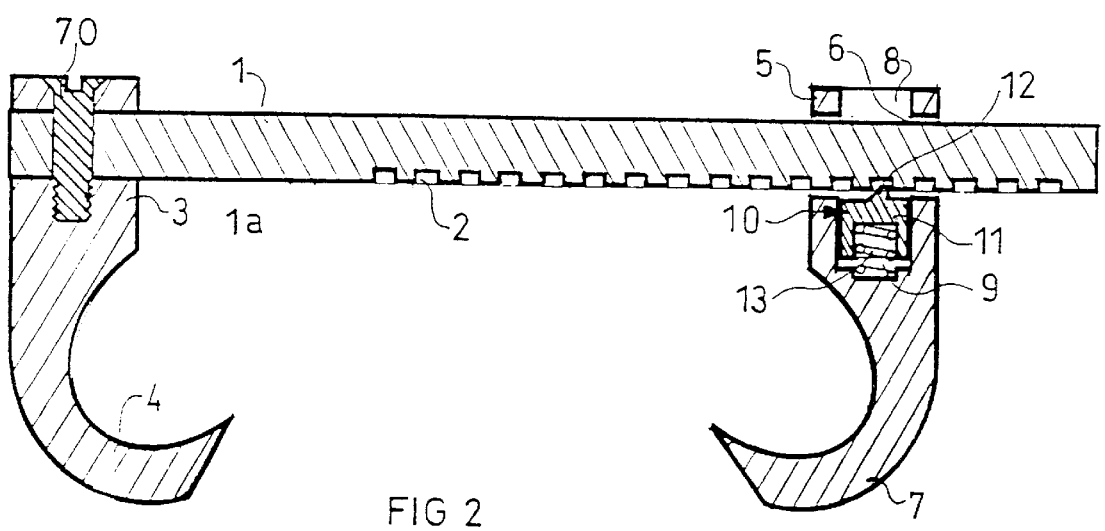
FIG. 2 is a longitudinal section of it through an axial plane.

As shown in FIG. 2, the union of the bar 1 and linking means is ensured by means of a headless screw 70 introduced into a threaded bore arranged axially in the cylindrical body 3 and transversally in said bar 1.

Such an embodiment of union has the advantage of making it possible, in an emergency, to separate the linking means from the bar 1 rapidly, and thus to allow a rapid removal of the osteosynthesis device. In addition, it enables the orientation of the hook 4 to be reversed depending on the use envisaged.

As represented in FIGS. 1 to 4, these attachment devices are, in addition, disposed so that the hook 4 extends in the prolongation of the notched face 1*a* of the bar 1.

The movable part of this osteosynthesis device, designed to be moved along the bar 1, has an external form similar to that of the means for attachment of the fixed part and hence comprises a cylindrical body 5 drilled with a radial bore 6 forming a sleeve of cross-section appreciably greater than that of the bar 1 adapted to produce a clearance between said body and bar, and an attachment piece in the form of a hook 7 extending in the prolongation of said body.

In addition, a longitudinal bore 8 is drilled through the body 5 from the end face of this body 5 opposite to the hook 7 so as to form opposite to said end face with respect to the radial bore 6, a cylindrical housing 9 opening radially into said radial bore.

Furthermore, this movable part comprises a ratchet system arranged to be accommodated in the housing 9 of the cylindrical body 5, and adapted to interlock with the notches 2 of the bar 1 so as to form with these latter a one-way locking mechanism.

This ratchet system comprises, in the first place, a hollow pawl 10 sealed by an upper wall 11 from which projects an asymmetrical tooth 12 with an inclined face 12*a* at a slope of about 45 degrees with respect to said upper wall, and a blocking face 12*b* at right angles to this upper wall.

In addition, the portion 11*a* of this upper wall 11 adjacent to the inclined face 12*a* of the asymmetric tooth 12 extends at a lower level than that of the portion 11*b* of said upper wall adjacent to the blocking face 12*b* of said asymmetrical tooth. As an example the difference in level between the portions 11*a*, 11*b* of the surface is for example of the order of two to three tenths of a millimeter.

Finally, the ratchet system comprises a helicoidal spring 13 accommodated inside the pawl 10 so as to be supported under the upper face 11 of this latter and on the bottom wall of the housing 9 and to engage said ratchet system in its locking position.

Figure 3:
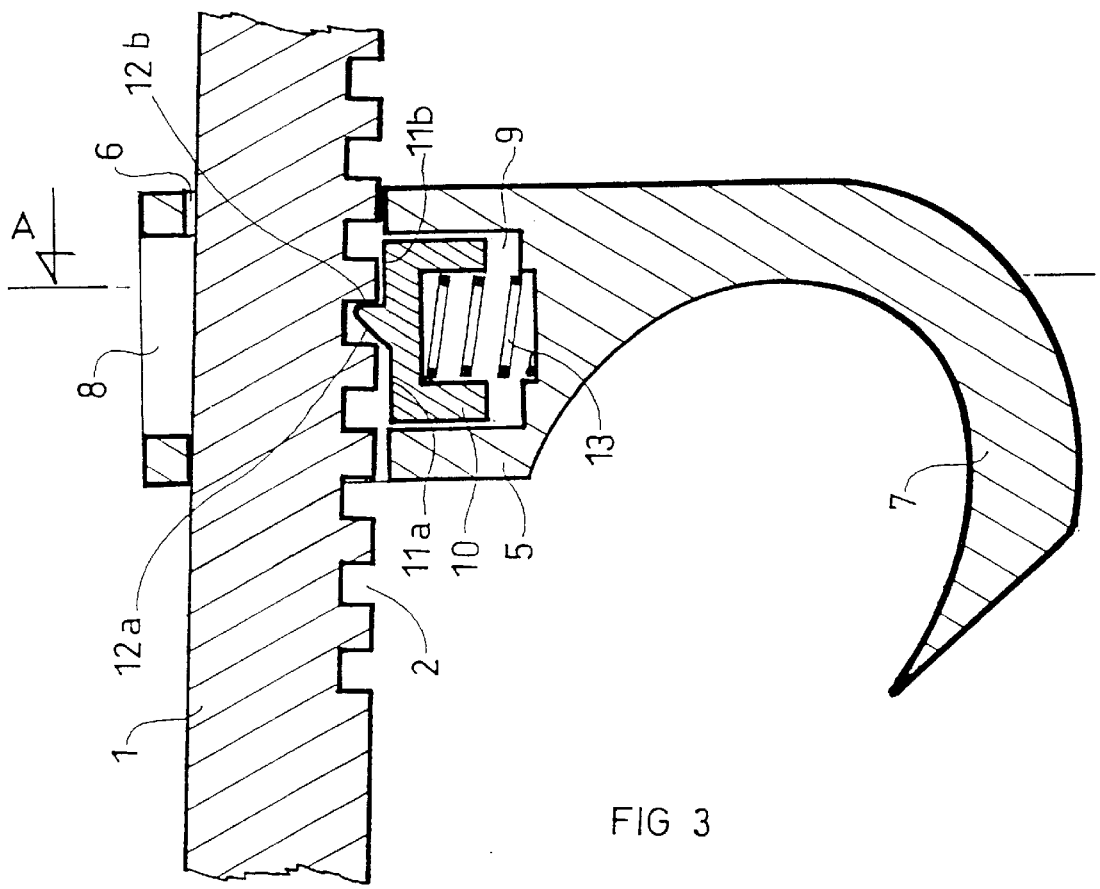
FIG. 3 is an enlarged partial longitudinal section representing the movable part in its self-locking position.
Figure 4:
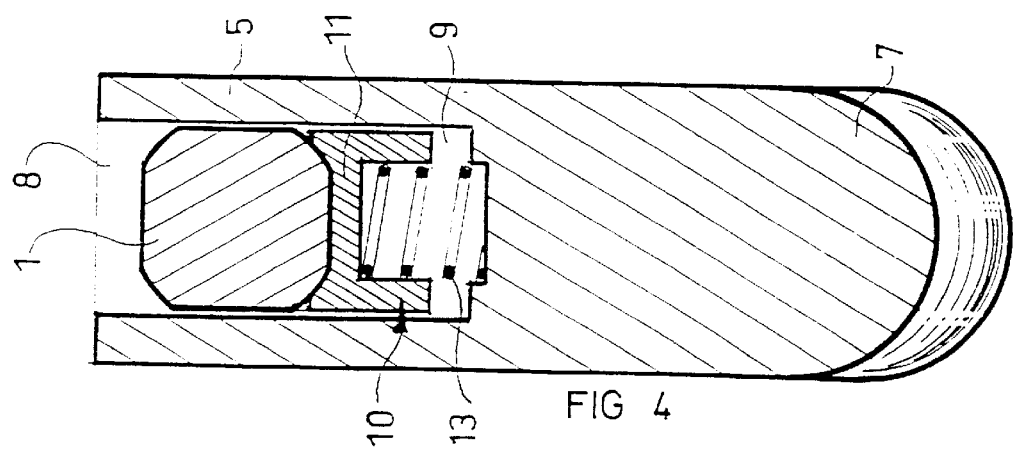
FIG. 4 is an enlarged transverse section of it through a plane A.

As represented in FIG. 3, owing to the clearance of the mounting existing between the bar 1 and the cylindrical body, this latter is induced to swivel into its locking position, this swivelling being in addition limited on account of the difference in level of the upper face 11 of the pawl 10, leading to the production of a wedge effect and hence to a self-locking when effort is applied to the movable part. Consequently, effort does not influence the asymmetric tooth 12 which thus has the function of only ensuring the maintenance of the movable part in position.

It should be noted that the device shown in FIGS. 1 to 4 is designed for a compressive osteosynthesis (locking tending to prevent the hooks 4, 7 from moving apart). However, this device may also be used for the purpose of a distractive osteosynthesis by the simple reversal of the position of the movable part and linking means.

Figure 5:
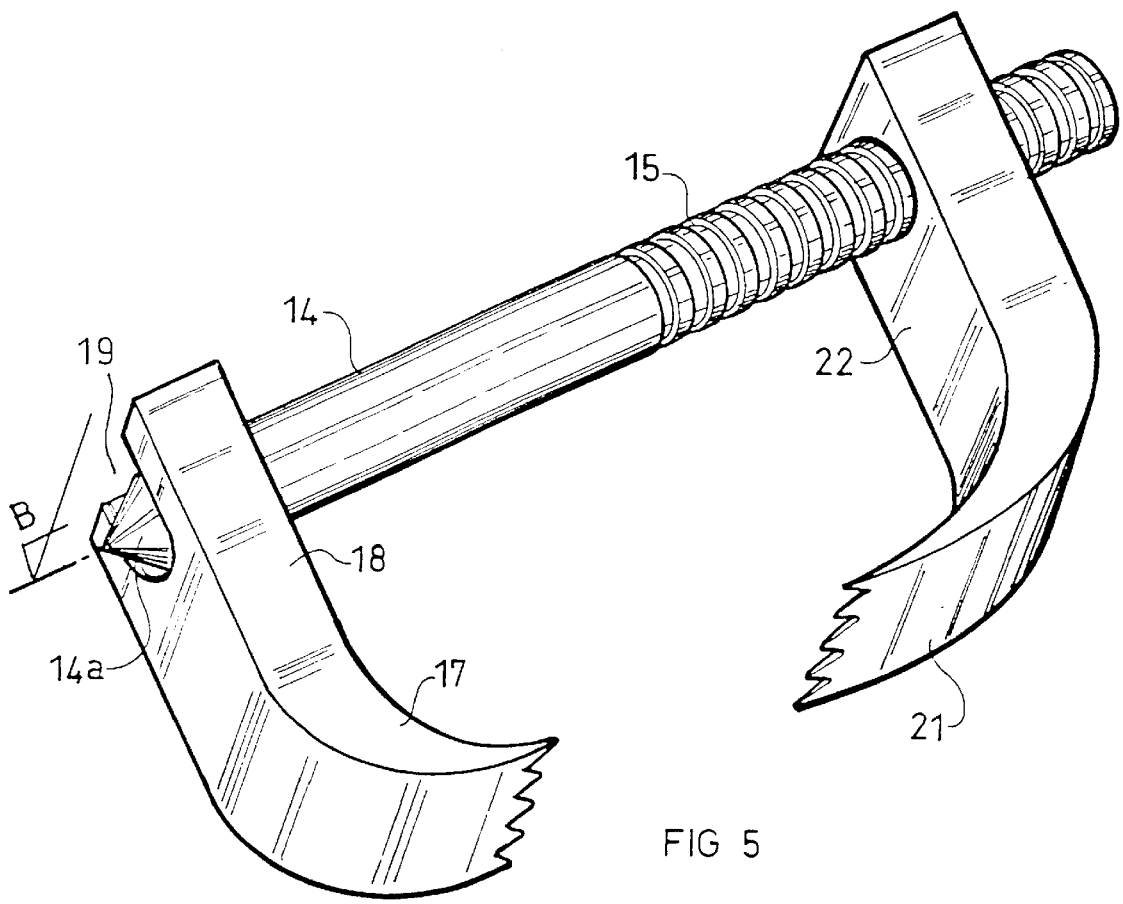
FIG. 5 is a perspective view of a second embodiment of an osteosynthesis device in conformity with the invention designed for a trochanter or olecranal osteosynthesis.
Figure 6:
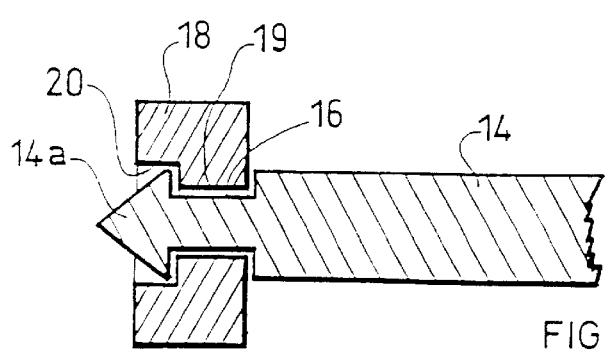
FIG. 6 is a partial longitudinal section through a plane B.

The second osteosynthesis device represented in FIGS. 5, 6 is designed in particular for a trochanter or olecranal osteosynthesis.

The fixed part of this osteosynthesis device comprises a spindle fitted with a pointed end 14*a* and possessing annular notches 15 over a portion of its length starting from the opposite end.

In addition, this spindle 14 comprises an annular bearing 16 longitudinally juxtaposed to its pointed end 14*a*.

This fixed part comprises in addition an attachment piece having the form of a clamp 17 extending in the prolongation of a body 18 in a rectangular parallelepiped form.

In order to ensure the relative positioning of this attachment device and the spindle 14, this latter comprises a transverse channel 19 recessed into the end face of the body 18 capable of being accommodated in the annular groove of said spindle.

Furthermore, as shown in FIG. 6, this channel 9 possesses longitudinally a counterbore 20 of cross-section adapted so that it partially masks the pointed end 14*a*.

In view of the shortness of the pointed end 14*a*, this counterbore 20 makes it possible to prevent, by partially masking this latter, having to section it at the end of the operation.

The movable part of this osteosynthesis device possesses an external form similar to that of the attachment device 17, 18 of the fixed part. It is thus constituted of a clamp 21 forming the prolongation of a rectangularly parallelepiped shaped body 22 through which is drilled a bore of cross-section adapted to that of the spindle 14, this body 22 incorporating a ratchet system identical with that described with reference to FIGS. 1 to 4.

Figure 7:
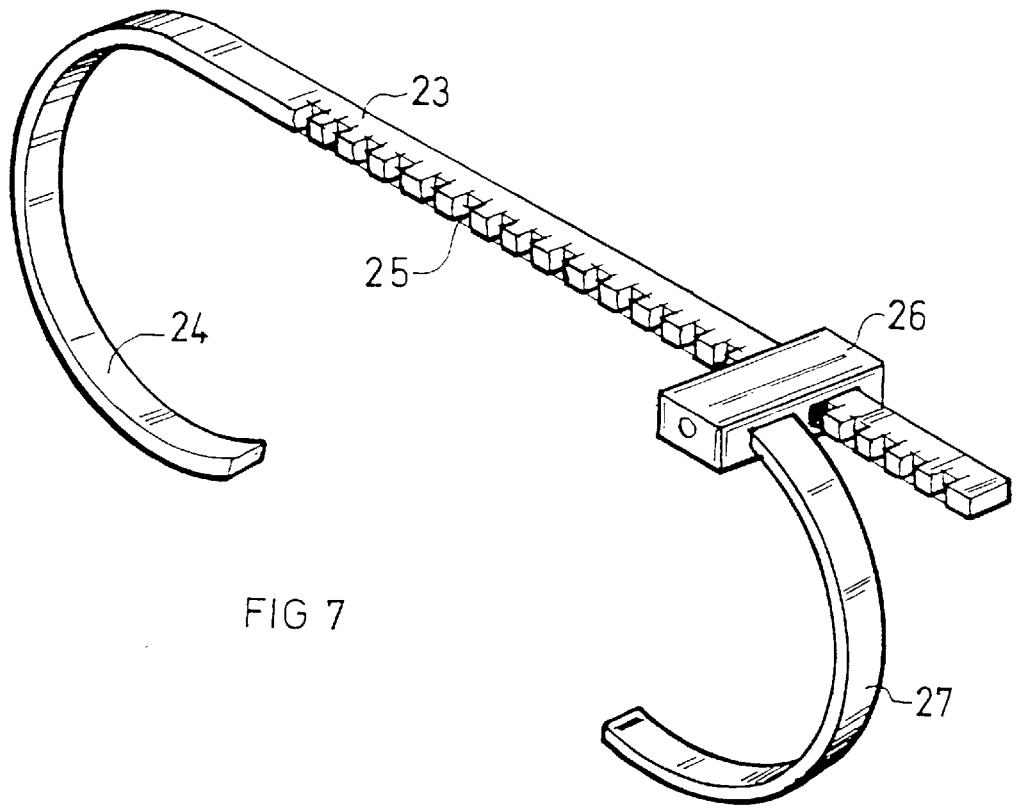
FIG. 7 is a perspective view of a third embodiment of an osteosynthesis device in conformity with the invention designed for a long bone or sternum osteosynthesis.

The osteosynthesis device shown in FIG. 7 is designed in particular for the osteosynthesis of long bones (tibia, femur, humerus, . . . ) as well as for osteosynthesis of the sternum.

The fixed part of this osteosynthesis device comprises a rectilinear rigid blade 23 of rectangular cross-section (for example 4 mm wide and 2 mm thick) curved at one end so as to form a bend 24 of 180 degrees. Starting from the opposite end and over approximately three quarters of its length this rigid blade comprises a number of notches 25 arranged on one edge of this latter.

As for the movable part of this osteosynthesis device, it comprises a body 26 of thin rectangular parallelepiped form, through which is drilled transversally a bore of rectangular cross-section adapted to that of the rigid blade 23. As previously, this body 26 incorporates a one-way locking ratchet system of the fixed and movable parts.

This movable part comprises, in addition, an attachment piece constituted of a bent rigid blade 27 forming a bend of 180 degrees, one of the ends of which is crimped or soldered onto the body 26 in the region of one of the longitudinal lateral faces of this latter.

As shown in FIG. 7, the attachment devices 24, 27 of the fixed and movable parts are thus displaced laterally and ensure perfect clamping on the bone.

Figure 8:
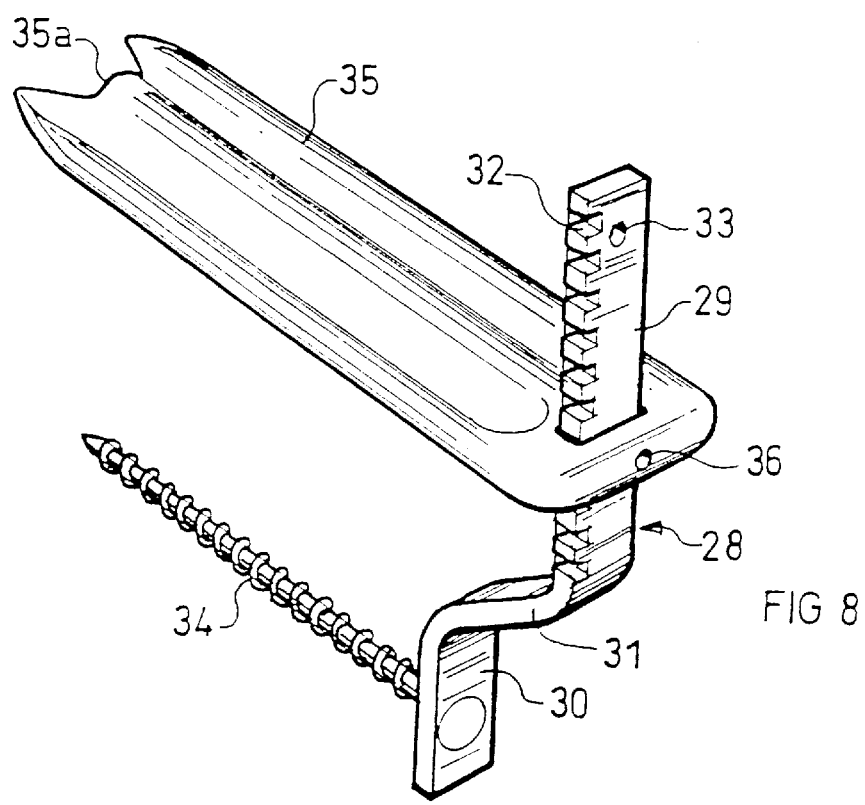
FIG. 8 is a perspective view of a fourth embodiment of an osteosynthesis device in conformity with the invention designed for performing osteotomies.

The osteosynthesis device shown in FIG. 8 is designed in particular for performing osteotomies.

The fixed part of this osteosynthesis device is constituted of a rigid blade 28 of rectangular cross-section and shaped longitudinally to adapt to the form of an epiphysis. For this purpose this rigid blade 28 comprises two rectilinear and parallel end sections 29, 30 connected by a central section 31 inclined with respect to the longitudinal axis of these latter.

In addition, the upper end section 29 designed to be contraposed against an epiphysis has an edge in which are arranged a number of notches 32. An aperture 33 is also drilled through this upper section 29 and arranged close to its upper end designed for the introduction of a guiding pin.

An aperture able to accommodate the head of a screw 34 is drilled through the lower section.

The movable part of this osteosynthesis device itself comprises a plate 35 of conventional design equipped with a cutting end edge 35*a*. Towards its opposite end, this plate 35 comprises a transverse slot adapted to make it possible to mount it on the fixed part, in respect to which is incorporated a ratchet system in conformity with the invention.

Finally, this plate 35 comprises a transverse longitudinal bore 36 arranged to allow the alignment of this latter by means of a guiding pin when it is implanted.

Figure 11:
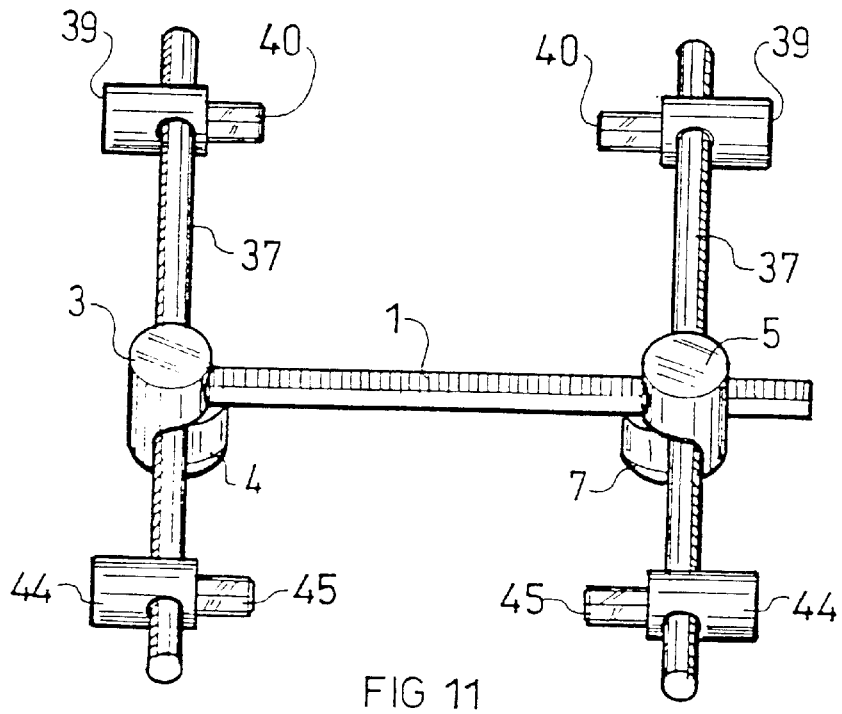
FIG. 11 is a partially skewed plan view of a seventh embodiment of an osteosynthesis device in conformity with the invention also designed for spinal surgery.

The osteosynthesis devices shown in FIGS. 9, 10 and 11 are all three designed for spinal surgery.

In the first place, the osteosynthesis device shown in FIG. 9 is designed to allow a one stage assembly comprising two points of anchoring.

The fixed part of this osteosynthesis device comprises a rectilinear bar 37 equipped with a flat longitudinal face in which are arranged a number of notches 38.

This fixed part comprises, in addition, means of linkage comprising a cylindrical body 39 through which is drilled a radial bore of cross-section adapted to the bar 37, able to make it possible to assemble it on this latter, and an axis 40 of polygonal cross-section in the axial extension of said body.

As shown in FIG. 9, these linkage means are designed to be combined with a pedicular anchoring screw 41 fitted with a head 42 through which is drilled a slot 43 of polygonal cross-section adapted to that of the axis 40. As an example, this slot 43 and hence the axis 40 may be octogonal or form an indentation known by the designation "TORQ".

In addition, the previously mentioned linking means may be either fixed in relation to the bar 37 or be fitted with a ratchet system in conformity with the invention allowing their translation in only one direction of displacement.

As for the movable part of this osteosynthesis device, it has the same structure as that of the linking means of the fixed part and thus comprises a cylindrical body 44 incorporating a ratchet system and an axis 45 of polygonal cross-section able to be combined with a pedicular screw such as described above.

In addition to the inherent advantages in the design of the osteosynthesis devices according to the invention, the value of such an osteosynthesis device is in providing a number of rotational adjustments in the sagittal plane.

The osteosynthesis device shown in FIG. 10 has the same basic design as that described above but it is designed to allow a multi-stage assembly with three anchoring points. (For the purposes of simplification, the same numerical references will therefore be used to designate similar elements).

This osteosynthesis device comprises a fixed unit constituted of two bars 37 each combined with means of linkage composed of a cylindrical body 39 and a polygonal axis 40, said bars being arranged in parallel, being positioned back to front and displaced longitudinally with respect to each other.

As for the movable part it comprises two cylindrical bodies 46, 47 each mounted on a bar 37 and each incorporating a ratchet system, said bodies being connected by a transverse axis 48 of polygonal cross-section.

This movable part is designed to be combined with a pedicular screw 49 fitted with a head 50 having a sleeve 51 of polygonal cross-section adapted to that of the axis 48 and an external thread 52 in the upper part and a cap 53 capable of being screwed onto said head after the screw has been placed in position on the axis 48.

The osteosynthesis device shown in FIG. 11 makes it possible to perform a framework assembly.

It comprises two osteosynthesis devices in conformity with those described with reference to FIG. 9, the bars 37 of which are assembled in parallel and are connected by an osteosynthesis device in conformity with that described with reference to FIGS. 1 to 4, the hooks 4, 7 of which operate in unison with said bars.

Figure 12:
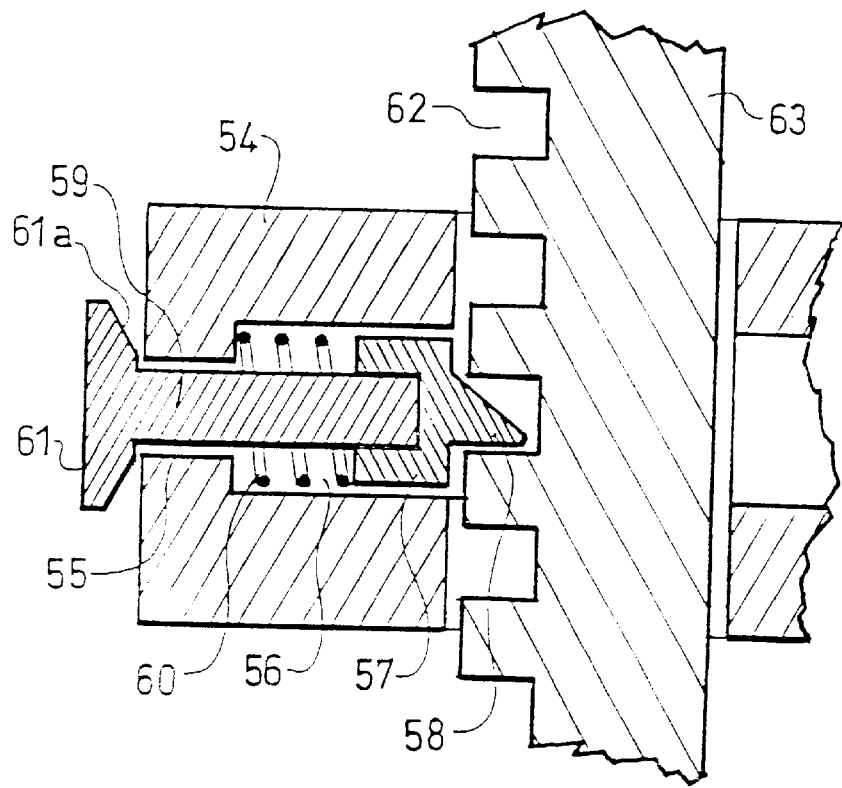
FIG. 12 is an enlarged partial longitudinal section illustrating a variant of the embodiment of the ratchet system of an osteosynthesis device in conformity with the invention.

Finally, FIG. 12 presents a variant of a ratchet system in conformity with the invention.

According to this variant, the body 54 of the movable part of the osteosynthesis device comprises a bore 55 opening into the bottom of the housing 56 of the ratchet system and in the region of one of the external faces of said body, respectively, and possessing a cross-section smaller than that of the said housing.

The ratchet system comprises a pawl 57 equipped with a front face having an inclined asymmetrical tooth 58 extended at the opposite side to said front face by an axis 59 around which is mounted a spring 60, said axis being adapted to extend into the bore 55 and open towards the exterior of the body 54.

Furthermore, this axis 59 is fitted at its emergent end with a control device 61 exhibiting opposite the external face of the body 54 a bevelled frontal face 61*a* able to make it possible to cause the ratchet system to recoil by means of an appropriately formed tool.

Such a variant has the advantage of making it possible to reverse very readily the permitted direction of displacement of the osteosynthesis device by a simple rotation through 180 degrees of the ratchet system, once the latter has recoiled so as to disengage the asymmetric tooth from the notches 62 of the elongated element 63 of the fixed part.

As a consequence, the same device may be used, without needing to be dismantled, for distractive and compressive osteosyntheses. In addition, such a variant has an appreciable usefulness for operations such as an osteotomy where the bony parts must be separated in a first phase and then be compressed in a second phase.

We claim:

1. Implantable osteosynthesis device comprising:

a fixed part comprised of an elongated element;

a movable part movable relative to the fixed part, and comprised of a body which forms a sleeve capable of sliding along the elongated element; and coupling means adapted to block translation of said parts so as to obtain a clamping effect on a bone, said coupling means comprised of one-way locking means coupled or incorporated respectively in one of the fixed or movable parts and arranged on the other part to allow the relative displacement of said parts in only one direction for providing the clamping effect and to lock in translation the fixed and movable parts in the other direction;

said one-way locking means having a number of parallel notches arranged along the elongated element of the fixed part and a ratchet system incorporated in the body of the movable part, said ratchet system comprising an asymmetric tooth operatively arranged with elastic means and adapted to be accommodated in the notches of the elongated element, the notches and the tooth being structured and arranged so that when the tooth is accommodated in one of the notches there is a clearance between an outer surface of the tooth and an inner surface of the notch enabling the ratchet system and the body to tilt with respect to said elongated element and produce a wedge effect ensuring self-locking.

2. Osteosynthesis device according to claim 1, wherein the asymmetric tooth extends in projection with respect to an upper face of a pawl and has an inclined front face capable of displacing the movable part in one direction and an opposite front face for blocking translation of said movable part, a first portion of the upper face of the pawl adjacent to the inclined front face of the asymmetric tooth extending at a lower level than a second portion of said upper face adjacent to the opposite front face of said asymmetric tooth.

3. Osteosynthesis device according to claim 1, wherein the body of the movable part comprises a housing having a bottom and opening radially into the sleeve.

4. Osteosynthesis device according to claim 3, further comprising a bore arranged transversely with respect to the sleeve, said bore being drilled through the body of the movable part from an external face of said body so as to form opposite said external face with respect to the sleeve the housing of the ratchet system.

5. Osteosynthesis device according to claim 3, further comprising:
   a bore arranged transversely with respect to the sleeve, said bore being drilled through the body of the movable part from an external face of said body so as to open into the bottom, said bore having a cross section smaller than that of the housing;
   the ratchet system having opposite to the asymmetric tooth, an axis which extends into the bore, said axis having an end which emerges outside of the body of the movable part, and said end being fitted with a control device adapted to swivel on itself.

6. Osteosynthesis device according to claim 1, wherein:
   the elongated element comprises a rectilinear bar and the coupling means comprise a part forming a piece with one end of the rectilinear bar and an attachment piece extending in prolongation of said part and having the form of a hook;
   the movable part comprises an attachment piece extending in prolongation of the body of said movable part and having a similar hook form, and arranged to extend in parallel with the fixed part.

7. Osteosynthesis device according to claim 6, wherein the rectilinear bar comprises longitudinally at least one flat face, the sleeve arranged in the body of the movable part having a cross-section coupled to that of said rectilinear bar.

8. Osteosynthesis device according to claim 1, wherein:
   the elongated element is constituted of a rectilinear rigid blade extending in a longitudinal axis and curved at one of its ends so as to form a first bend of 180 degrees;
   the movable part comprises an attachment device borne by the body of said movable part and constituted of a curved rigid blade forming a second bend of 180 degrees coupled to the rigid blade, and arranged so as to extend in parallel therewith, said second bend being laterally displaced with respect to the longitudinal axis of the elongated element.

9. Osteosynthesis device according to claim 1, wherein:
   the elongated element is constituted of a cylindrical spindle having a pointed end, an annular bearing close to said pointed end and a first attachment piece having the form of a claw fitted with a body having a transverse groove for accommodating the annular bearing of the spindle;
   the movable part comprises a second attachment piece extending in prolongation of the body of said movable part and having a similar claw form, and arranged to extend in parallel to the fixed part.

10. Osteosynthesis device according to claim 9, wherein the transverse groove has longitudinally a counterbore of cross-section adapted to partially cap the pointed end of the spindle adjacent to the annular bearing.

11. Osteosynthesis device according to claim 1, wherein:
   the elongated element is constituted of a rigid blade exhibiting two parallel and rectilinear end sections connected by a central section inclined with respect to the longitudinal axis of the end sections, one of said end sections having an aperture for accommodating a screw head and the other end section being equipped with locking means; and
   the moveable part comprises at least one attachment piece capable of penetrating a bone.

12. Osteosynthesis device according to claim 1, wherein:
   the elongated element is constituted of a rectilinear bar, and linking means comprising a body member mounted on said elongated element prolonged by an axis of polygonal cross-section, and a first attachment piece consisting of a first pedicular screw fitted with a head through which is drilled a slot of polygonal cross-section corresponding to the cross-section of the axis of the body member;
   the movable part includes linking means comprising an axis of polygonal cross-section extending in prolongation of the body of said movable part, in parallel with the axis of the linking means, and a second attachment piece consisting of a second pedicular screw fitted with a head through which is drilled a slot of polygonal cross-section corresponding to the cross-section of the axis of the linking means.

13. Osteosynthesis device according to claim 12, further comprising:
   a fixed unit composed of two fixed parts, each comprising an elongated element constituted of a rectilinear bar and linking means comprising a body member mounted on said elongated element near one of its ends, extended by an axis of polygonal cross-section and a third attachment piece consisting of a third pedicular screw fitted with a head through which is drilled a slot of polygonal cross-section corresponding to the cross-section of the axis of the body member;
   an intermediate movable unit linking the elongated elements of the fixed unit in a region of a section of the elongated elements opposite the end bearing the linking means, said intermediate movable unit being structured and arranged so that the elongated elements extend in parallel while being partially displaced longitudinally, said intermediate movable unit comprising a movable part mounted on each elongated element and a linking unit comprising a transverse axis of polygonal cross-section connecting bodies of the movable parts and extending at right angles with respect to the elongated elements, and a securing piece consisting of a pedicular screw fitted with a head having a groove of polygonal cross-section corresponding to the cross-section of the transverse axis and an external thread in the upper part, and a cap for screwing onto the upper part of said head.

14. Osteosynthesis assembly comprising in combination two osteosynthesis devices in accordance with claim 12, arranged in parallel, and a third osteosynthesis device structured and arranged so as to connect the elongated elements of the two osteosynthesis devices, and to form a framework therewith.

15. Osteosynthesis device according to claim 12, wherein the body member of the linking means of each fixed part comprises one-way locking means capable of making it possible to displace said body member in only one direction relative to the corresponding elongated element.

* * * * *